(12) United States Patent
Kelly

(10) Patent No.: US 9,956,095 B2
(45) Date of Patent: May 1, 2018

(54) SELF-EXPANDING BRIDGING STENT WITH ANCHORING PROJECTIONS AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

(*) Notice: Subject to any disclaimer, the term of this patent is extended or adjusted under 35 U.S.C. 154(b) by 0 days. days.

(21) Appl. No.: 15/229,788

(22) Filed: Aug. 5, 2016

(65) Prior Publication Data

US 2017/0035587 A1 Feb. 9, 2017

Related U.S. Application Data

(60) Provisional application No. 62/201,549, filed on Aug. 5, 2015.

(51) Int. Cl.
| | | |
|---|---|---|
| *A61F 2/24* | (2006.01) | |
| *A61F 2/848* | (2013.01) | |
| *A61F 2/07* | (2013.01) | |
| *A61F 2/966* | (2013.01) | |
| *A61F 2/97* | (2013.01) | |

(Continued)

(52) U.S. Cl.
CPC ............... *A61F 2/848* (2013.01); *A61F 2/07* (2013.01); *A61F 2/844* (2013.01); *A61F 2/962* (2013.01); *A61F 2/966* (2013.01); *A61F 2/97* (2013.01); *A61F 2002/8483* (2013.01); *A61F 2002/8486* (2013.01); *A61F 2002/9505* (2013.01);

(Continued)

(58) Field of Classification Search
CPC .......... A61F 2/844; A61F 2/848; A61F 2/962; A61F 2/966; A61F 2/97; A61F 2002/8483; A61F 2002/8486; A61F 2002/9665

See application file for complete search history.

(56) References Cited

U.S. PATENT DOCUMENTS

| | | | |
|---|---|---|---|
| 2006/0190070 A1* | 8/2006 | Dieck ....................... | A61F 2/90 623/1.12 |
| 2012/0130470 A1* | 5/2012 | Agnew ..................... | A61F 2/86 623/1.11 |

(Continued)

FOREIGN PATENT DOCUMENTS

| | | |
|---|---|---|
| EP | 2110102 A1 | 10/2009 |
| WO | 06/091891 A2 | 8/2006 |

(Continued)

OTHER PUBLICATIONS

International Search Report for corresponding PCT application No. PCT/US2016/045790 dated Oct. 14, 2016.

*Primary Examiner* — Robert Lynch
(74) *Attorney, Agent, or Firm* — McDonnell Boehnen Hulbert & Berghoff LLP

(57) ABSTRACT

The present disclosure provides a stent graft comprising (a) a self-expandable stent structure having a first end and a second end, wherein the self-expandable stent structure defines a lumen, (b) at least one restraint configured to be coupled to an exterior surface of the stent graft in a compressed condition, and wherein the at least one restraint is configured to be broken to permit the stent graft to transition to an expanded condition, and (c) a first plurality of anchoring projections coupled to the exterior surface of the stent graft adjacent to the first end of the self-expandable stent-structure.

11 Claims, 3 Drawing Sheets

(51) Int. Cl.
    *A61F 2/844*     (2013.01)
    *A61F 2/962*     (2013.01)
    *A61F 2/95*      (2013.01)
(52) U.S. Cl.
    CPC ............... *A61F 2002/9665* (2013.01); *A61F 2250/0071* (2013.01)

(56) References Cited

U.S. PATENT DOCUMENTS

2012/0179086 A1* 7/2012 Shank ................. A61F 2/04
                                            604/8
2014/0277562 A1* 9/2014 Seddon ................ A61F 2/915
                                            623/23.7

FOREIGN PATENT DOCUMENTS

| WO | 11/067764 A1 | 6/2011 |
| WO | 13/182614 A1 | 12/2013 |
| WO | 14/020609 A1 | 2/2014 |

\* cited by examiner

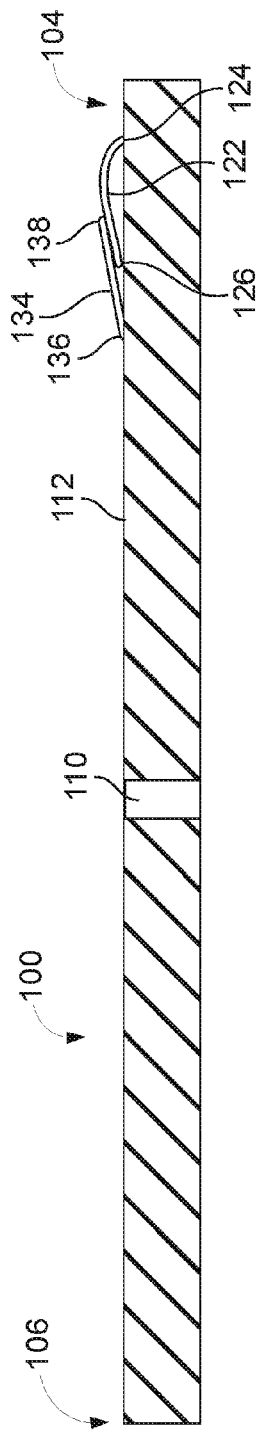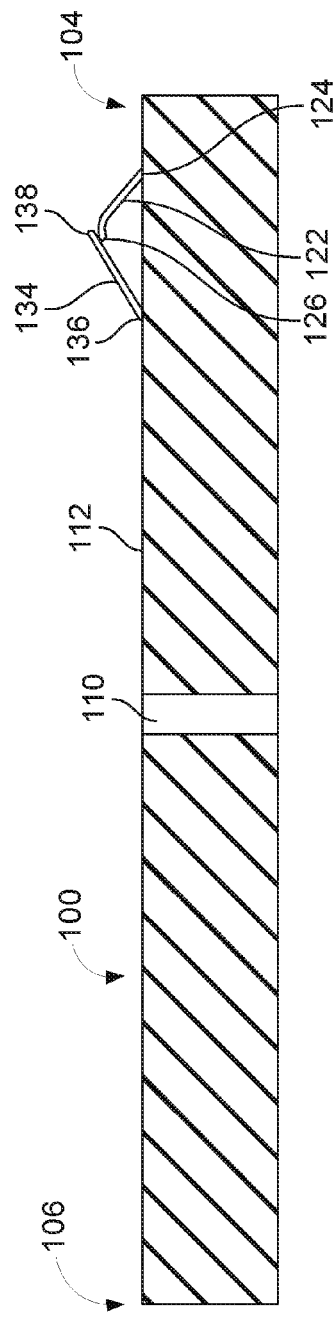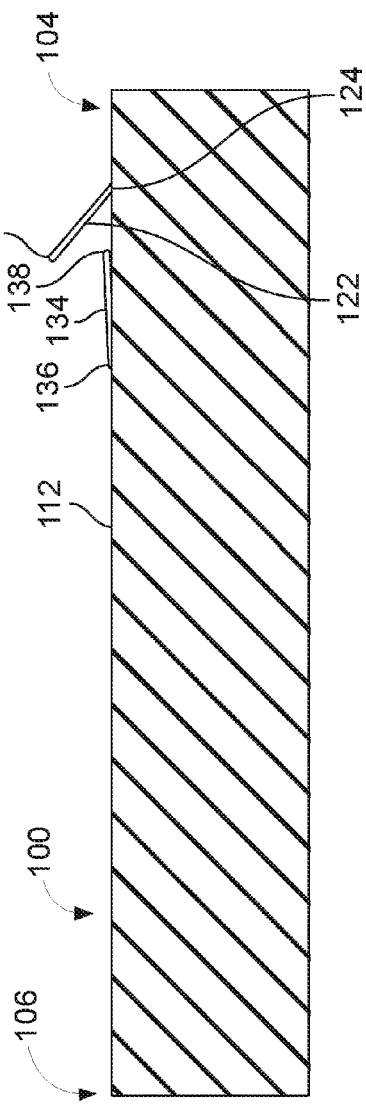

SELF-EXPANDING BRIDGING STENT WITH ANCHORING PROJECTIONS AND METHODS FOR USE

RELATED APPLICATIONS

This application claims priority to U.S. Provisional Application No. 62/201,549 entitled "Self-Expanding Bridging Stent with Anchoring Projections at Distal & Proximal Ends," filed on Aug. 5, 2015, which is hereby incorporated by reference in its entirety.

BACKGROUND THE INVENTION

Self-expanding stent grafts are generally flexible and resistant to kinking. The shape memory properties of self-expanding stent grafts also help them to avoid undergoing permanent deformations. For bridging stents, self-expanding stent structures can be problematic, because the delivery catheter typically needs to be pulled back over the stent to release the stent. The action of pulling back the delivery catheter can result in the stent being dislodged from the target vessel. Also, the amount of chronic outward radial force required for fixation found most often in a balloon expandable stent graft can cause stenosis formation because of a sharp compliance transition.

Active fixation relates to suprarenal portions of abdominal aneurysm stent grafts, but active fixation is achieved by a mechanism tied to the central core of the delivery system. Traditionally, active fixation includes traumatic hooks that are released by actuating a button on the delivery system. This mechanism may be quite bulky and so it can only be used in main body aortic components. The delivery catheter required in such an example is 20 French, which is much larger than the 7 French catheters used with bridging stents.

Passive fixation refers to a securement technique between a stent graft and arterial structure such that fixation through puncture of the arterial structure is avoided. Instead, passive fixation is often achieved through chronic outward radial force of the stent itself Chronic outward radial force is the outward radial force created when an oversized stent or stent graft is placed within an arterial structure. Chronic outward radial force may be problematic for several reasons. For example, in an aortic application, chronic outward radial force may potentially cause aneurysmal growth. In addition, chronic outward radial force applied in a smaller branched vessel may result in extensive stretch at the transition from covered to the uncovered vessel. This stretch can cause damage that leads to vessel narrowing or neointimal hyperplasia. This phenomena can also be referred to as "edge stenosis."

SUMMARY OF THE INVENTION

The bridging stent graft disclosed herein may be used to exclude an aneurysm from a previously deployed stent graft to a native branch vessel spanning empty aneurysmal sac. Such a deployment may place new demands on small- or medium-sized stent grafts. For instance, the ends of the stents may be at risk of becoming dislodged, resulting in catastrophic hemodynamic instability. While adequate fixation may be achieved with excess outward radial force, this excessive force can cause problematic narrowing of the artery. Fixation at both ends of the stent graft may be achieved by way of appropriate compliance interfaces in the form of a plurality of anchoring projections. The various embodiments of the plurality of anchoring projections may increase the friction between the bridging stent and any previously-placed or subsequently-deployed stent graft to increase active fixation.

The present bridging stent graft may allow for active fixation in self-expanding stent grafts without the need for central core actuation. Further, the present bridging stent graft may allow for active fixation in the target branch vessel with a self-expandable stent graft without elevated chronic outward radial force increasing predictability and durability in deployment as well as providing acceptable fixation without a compliance transition.

Thus, a first aspect of the disclosure provides a stent graft comprising (a) a self-expandable stent structure having a first end and a second end, where the self-expandable stent structure defines a lumen, (b) at least one restraint coupled to an exterior surface of the stent graft in a compressed condition, and wherein the at least one restraint is configured to be broken to permit the stent graft to transition to an expanded condition, and (c) a first plurality of anchoring projections coupled to the exterior surface of the stent graft adjacent to the first end.

A second aspect provides a method for placement of a stent graft that includes: (a) introducing a guidewire into an arterial configuration via arterial access, (b) loading a delivery catheter containing the stent graft of the first aspect onto the guidewire, (c) moving the delivery catheter along the guidewire and introducing the delivery catheter into the arterial configuration via arterial access, and (d) deploying the stent graft into at least one of the arterial configuration and a lumen of a previously-placed stent graft.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5 is a side view of a stent graft with a plurality of retention flaps in a compressed condition, according to an example embodiment.

FIG. 6 is a side view of the stent graft in a transition condition, according to the example embodiment of FIG. 5.

FIG. 7 is a side view of the stent graft in an expanded condition, according to the example embodiment of FIG. 5.

DETAILED DESCRIPTION OF THE INVENTION

Figure 1:
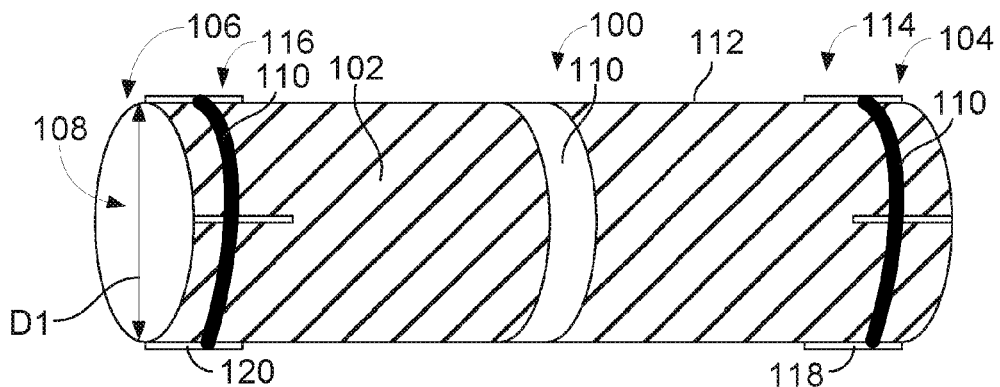
FIG. 1 is a side perspective view of a stent graft having a plurality of crimped stents in a compressed condition, according to an example embodiment.

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means +/−5%.

As used herein, diameter ranges pertain to an unconstrained, ex vivo state of the stent graft and stent graft extensions. When the stent graft and stent graft extensions are in a deployed, in vivo state the diameter ranges will be on the order of about 10-20% smaller in diameter than the ex vivo state.

As used herein, "first end" refers to the end of the stent graft that will be a "proximal end" upon deployment in vivo through which blood flow enters the lumen of the stent graft.

As used herein, "second end" refers to the end of the main body stent graft that will be a "distal end" upon deployment in vivo through which blood flow exits the lumen of the stent graft. The "second end" is the end of the stent graft relative to the removable sheath, such that the second end is the end that is initially unsheathed during deployment.

As used herein, "passive fixation" refers to friction, interaction between the cloth of the grafts, radial strength of the stent structure and blood pressure that holds separate stent grafts together at the site of overlap.

As used herein, "active fixation" refers to features coupled to a stent, graft, or stent graft that may actively engage vasculature or another stent graft, including hooks, bi-directional hooks, stent structure elements, anchors, staples, bio-activated adhesive, or a combination thereof, among other possibilities.

As used herein, a "stent graft" is a tubular, radially-expandable device comprising a fabric supported by a stent, and may be used to bridge aneurysmal arteries. As such, the term stent graft may be used herein to include bridging stent grafts. Such stent grafts and methods for their deployment and use are known to those of skill in the art. For example, vascular sheaths can be introduced into the patient's arteries, through which items, including but not limited to, guidewires, catheters and, eventually, the stent graft, may be passed.

As used herein, a "stent" is typically a cylindrical frame and means any device or structure that adds rigidity, expansion force, or support to a prosthesis, while "stent graft" refers to a prosthesis comprising a stent and a graft material associated therewith that forms a lumen through at least a portion of the length of the stent. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics. The stents can either have material properties necessary to exhibit either self-expanding or balloon-expanding characteristics.

Any suitable graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

As used herein, a "catheter" is an apparatus that is connected to a deployment mechanism and houses a medical device that can be delivered over a guidewire. The catheter may include a guidewire lumen for over-the-wire guidance and may be used for delivering a stent graft to a target lumen. A catheter can have braided metal strands within the catheter wall to increase structural integrity. The structural elements of the catheter tip can be bonded or laser welded to the braided strands of the catheter to improve the performance characteristics of the catheter tip.

As used herein, a "guidewire" is an elongated cable comprised of various biocompatible materials including metals and polymers. Guidewires may be used for selecting target lumens and guiding catheters to target deployment locations. Guidewires are typically defined as wires used independently of other devices that do not come as part of an assembly.

As used herein, "lumen" refers to a passage within an arterial structure, such as the pulmonary arteries, stent grafts or the passage within the tubular housings or catheters through which the guidewire may be disposed.

As used herein, "radially outward" refers to a direction away from a longitudinal axis of a lumen of a stent graft.

As used herein, "radially inward" refers to a direction towards a longitudinal axis of a lumen of a stent graft.

Figure 2:
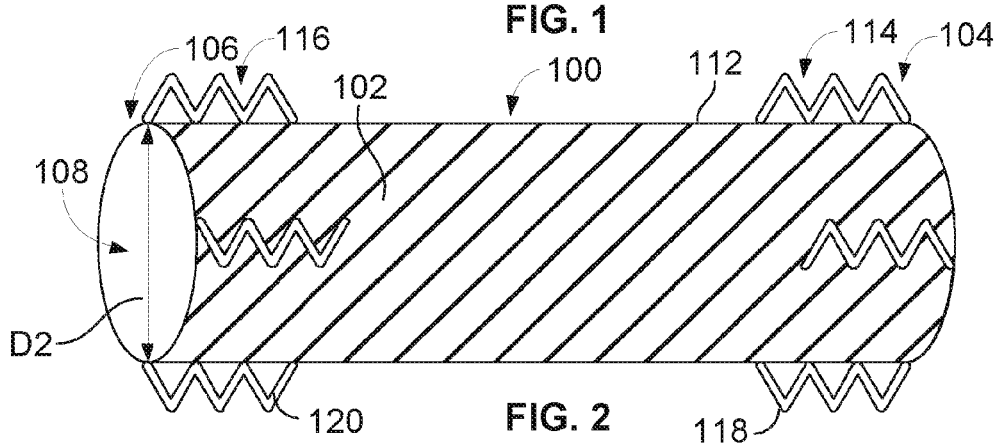
FIG. 2 is a side perspective view the stent graft in an expanded condition, according to the example embodiment of FIG. 1.

With reference to the Figures, FIG. 1 illustrates a stent graft 100 according to an example embodiment. The stent graft 100 includes a self-expandable stent structure 102 having a first end 104 and a second end 106. The self-expandable stent structure 102 defines a lumen 108. The stent graft 100 further includes at least one restraint 110 coupled to an exterior surface 112 of the stent graft 100 in a compressed condition. The restraint 110 is configured to be broken to permit the stent graft 100 to transition to an expanded condition, as shown in FIG. 2. The restraint 110 is described in more detail below. The diameter D1 of the stent graft 100 in the compressed condition is less than the diameter D2 of the stent graft 100 in the expanded condition. In various embodiments, the diameter D2 of the stent graft 100 in the expanded condition may range from about 4 mm to about 30 mm, and the length of the stent graft 100 may range from about 20 mm to about 250 mm.

The stent graft 100 further includes a first plurality of anchoring projections 114 coupled to the exterior surface 112 of the stent graft 100 adjacent to the first end 104 of the stent structure 102. In one example, the stent graft 100 further includes a second plurality of anchoring projections 116 coupled to the exterior surface 112 of the stent graft 100 adjacent the second end 106 of the stent structure 102. In one example, the first plurality of anchoring projections 114 may be structurally similar to the second plurality of anchoring projections 116 so as to have similar mechanical and material properties. In another example, the first plurality of anchoring projections 114 may be structurally different than the second plurality of anchoring projections 116 so as to have different mechanical and/or material properties. In yet another example, only the first plurality of anchoring projections 114 are present on the exterior surface 112 of the stent graft 100. In another example, the first plurality of anchoring projections 114 includes at least three anchoring projections, and the second plurality of anchoring projections 116 includes at least three anchoring projections.

The self-expandable stent structure 102 may comprise a plurality of woven nitinol wires. In such an example, the self-expandable stent structure 102 may further comprise textile fibers intermixed within the woven nitinol wires. In particular, textile fibers can be woven into the nitinol weave in opposing winds. The mix of the two can be optimized in such a way as to match the stretch and compliance of the artery the stent graft is designed to replace. In addition, the outer surface of the self-expandable stent structure 102 can be woven in such a way as to create a wear surface and discourage tissue ingrowth. The inner surface of the self-expandable stent structure 102 can be woven in such a way as to encourage tissue ingrowth to create the process of endothelialization. If the fibers on the inner surface of the self-expandable stent structure 102 may be woven in such a way as to align with the direction of blood flow it can further encourage endothelialization. For example, the woven textile filaments may expand when exposed to blood or when exposed to a second component for a binary polymer (e.g., growing a polymer on the stent structure), thereby filling in any gaps within the stent structure. In another example, the self-expandable stent structure 102 further may further comprise a polymer material intermixed within the woven nitinol wires. In yet another example, the self-expandable stent structure 102 comprises a plurality of layers of woven nitinol wires.

The restraint 110 may include (i) at least one polymer band, (ii) a polymer mesh, (iii) at least one biocompatible string, (iv) at least one cloth band, (v) a fracture point in the self-expanding stent structure 102, and/or (vi) an outer sheath 142 of a delivery catheter. The restraint 110 may help maintain the self-expandable stent structure 102 in the compressed condition during stent graft delivery to the target location. The restraint 110 may then be removed prior to or during expansion of the self-expandable stent structure 102. In one particular example, the restraint 110 may be broken by balloon expansion within the lumen 110 of the self-expandable stent structure 102, thereby releasing tension in the restraint 110 and permitting the self-expandable stent structure 102 of the stent graft 100 to expand. In operation, the restraint 110 may remain coupled to the stent graft 100 after being broken to prevent the restraint 110 from entering the blood stream. Alternatively, the broken restraint 110 may be captured between the exterior surface 112 of the stent graft 100 and a vessel wall. When the stent graft 100 is deployed in space (i.e., within the aneurysmal sack), the second end 106 may be deployed first and the restraint 110 may hold the self-expandable stent structure 102 closed until the balloon is deployed breaking the restraint 110 and thereby decoupling the restraint 110 from the stent graft 100. Such self-expanding stent graft structures may be less prone to kinking, and may be less prone to being radially deformed (because of shape memory properties) during subsequent stent placement and may be more flexible than balloon-expandable stent grafts. In various embodiments, the restraint 110 may extend the length of the stent graft 100, the restraint 110 may extend only between the first plurality of anchoring projections and the second plurality of anchoring projections 116, or may comprise three longitudinal bands 110, 140, 144 each covering one of the first plurality of anchoring projections 114, the second plurality of anchoring projections 116, and the approximate middle of the self-expandable stent structure 102, as a few examples.

Figure 3:
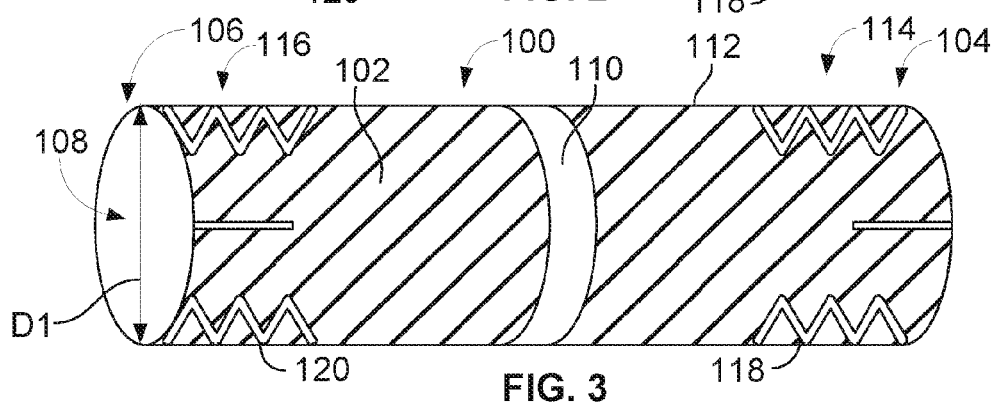
FIG. 3 a side perspective view a stent graft with one or more crimps in a compressed condition, according to an example embodiment.

The first plurality of anchoring projections 114 and/or the second plurality of anchoring projections 116 may take various forms. In one example, as shown in FIGS. 1-3, at least one of the first plurality of anchoring projections 114 or the second plurality of anchoring projections 116 is a longitudinally arranged stent having one or more crimps 118, 120. In such an example, the self-expandable stent structure 102 may be cut along one or more sides of the stent graft 100. In such an example, the one or more crimps 118, 120 may lie flat when the stent graft 100 is in the compressed condition, but may project radially away from the exterior surface 112 of the stent graft 100 when the stent graft 100 transitions to the expanded condition, thereby creating active interaction to either another stent graft or native tissue. In another example, the one or more crimps 118, 120 may not be part of the self-expandable stent structure 102, but may instead be separate components that are fixedly coupled to the exterior surface 112 of the stent graft 100.

As shown in FIG. 2, the crimped stents 118, 120 may extend radially outward when the stent graft is in the expanded condition. In particular, the crimped stents 118, 120 may extend radially outward a distance ranging from about 0.1 mm to about 3 mm from the exterior surface 112 of the stent graft 100 when the stent graft 100 is in the expanded condition. Foreshortening is a phenomenon that occurs in self-expanding stent grafts. While the stent graft 100 goes from the constrained state (i.e., compressed condition) to the unconstrained state (i.e., expanded condition), the stent graft 100 increases in diameter and decreases in length. This phenomenon may be used to actuate one or more crimped stents 118, 120.

In one example, as shown in FIG. 1, the crimped stents 118, 120 are flattened when the stent graft 100 is in the compressed condition. As such, the crimped stents 118, 120 may be substantially even with the exterior surface 112 of the stent graft 100 when the stent graft 100 is in the compressed condition, thereby minimizing the crossing profile when loading the stent graft 100 in a delivery catheter. The crossing profile refers to the diameter of the stent graft 100 in the compressed condition and the diameter of the delivery catheter combined. In another example, as shown in FIG. 3, the crimped stents 118, 120 extend radially inward when the stent graft 100 is in the compressed condition. In one example, as shown in FIG. 1, a restraint 110 covers at least one of the one or more crimps 118 of the first plurality of anchoring projections 114 or the crimped stents 120 of the second plurality of anchoring projections 116 when the stent graft 100 is in the compressed condition.

Figure 4:
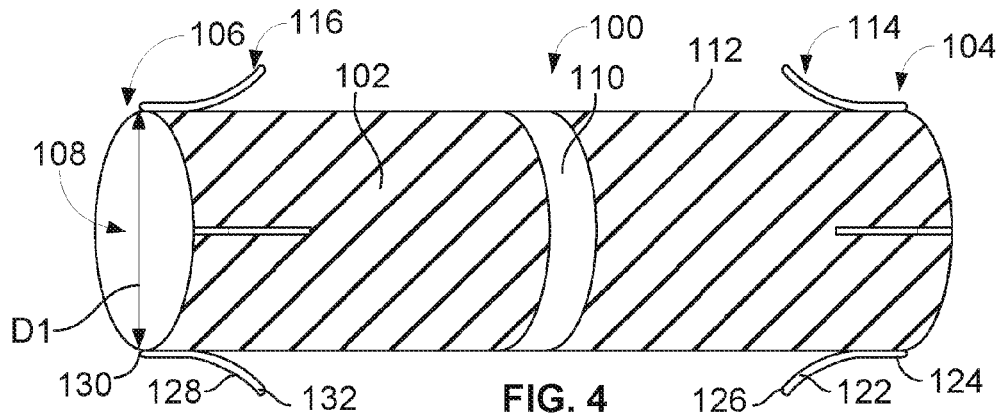
FIG. 4 is a side perspective view of a stent graft with a plurality of barbs in a compressed condition, according to an example embodiment.

In another example, as shown in FIG. 4, the first plurality of anchoring projections 114 includes a first plurality of barbs 122. In such an example, each of the first plurality of barbs 122 includes a fixed end 124 coupled to the exterior surface 112 of the stent graft 100 and a free end 126 directed toward the second end 106. In one optional embodiment, one restraint 110 may cover at least the free end 126 of each of the first plurality of barbs 122. The free end 126 of each of the first plurality of barbs 112 may extend a distance ranging from about 0.1 mm to about 3 mm from the exterior surface 112 of the stent graft 100 when the stent graft 100 is in the expanded condition.

In one example, the second plurality of anchoring projections 116 comprise a second plurality of barbs 128 with a fixed end 130 coupled to the exterior surface 112 of the stent graft 100 and with a free end 132 directed toward the first end 104. As such, each of the plurality of barbs 122, 128 extend toward the end of the stent graft 100 arranged opposite to the end that each respective barb 122, 128 is coupled to such that the barbs at the first end 104 essentially point in the direction of the barbs at the second end 106. In one example, each of the first plurality of barbs 122 and each of the second plurality of barbs 128 angle outward from the exterior surface 112 of the stent graft 100 from about 5 degrees to about 85 degrees when the stent graft 100 is in the expanded condition. In addition, each of the first plurality of barbs 122 and each of the second plurality of barbs 128 may be straight or curved when the stent graft 100 is in the expanded condition.

The first plurality of barbs 122 and the second plurality of barbs 128 may be made of a shape memory material, such as nitinol as an example. Further, the material of the first plurality of barbs 122 and the second plurality of barbs 128 may be sufficiently stiff to create some deformity of the receiving structure, allowing them to either create friction with or actively engage with the adjoining stent graft or to puncture the tissue of the target vessel (i.e., active fixation) when deployed within an artery, for example. The first plurality of barbs 122 and the second plurality of barbs 128 may be part of the self-expandable stent structure 102, or may be a separate component fixedly coupled to the exterior surface 112 of the stent graft 100. As such, the first plurality of barbs 122 and the second plurality of barbs 128 may be made of the same material as the self-expandable stent structure 102, or the first plurality of barbs 122 and the second plurality of barbs 128 may be made of a different material than the self-expandable stent structure 102. Each of the first plurality of barbs 122 and each of the second plurality of barbs 128 may be biased radially outward to hold the stent graft 100 in better apposition to the native vessel and to resist stent graft 100 pull out. In another embodiment, the first plurality of barbs 122 and/or the second plurality of barbs 128 may be used to aid in the cloth-to-vessel apposition.

In a further embodiment, the first plurality of barbs 122 and/or the second plurality of barbs 128 create both a positive fixation between the stent graft 100 and the native artery as well as with any additional bridging stent (thus helping to prevent stent separation). In particular, distal end fixation may be important as it helps keep the stent graft 100 from pulling out of the branch artery and the blood from being pumped into the aneurysmal sac. Blood flow into the aneurysmal sac could be catastrophic resulting in aneurysm rupture and requiring open surgical intervention to repair. To ensure the second end 106 of the stent graft 100 remains in the branch artery, active fixation is preferred. The second plurality of barbs 128 may be biased radially outward so as to traumatically engage with the tissue thereby anchoring the second end 106 in place.

The first end 104 of the stent graft 100 can also benefit from active fixation. In example embodiments for which the first end 104 will be placed in a previously-deployed stent graft, the first plurality of barbs 122 may be used to create active fixation. Active fixation helps prevent the stent graft 100 from being pulled out of the previously-deployed stent graft and may also allow for shorter stent structures to be employed on the stent graft 100 allowing for less aorta wall, for example, to be covered effectively minimizing the risk of paraplegia.

In one example, as shown in FIGS. 5-7, the stent graft 100 further includes a plurality of retention flaps 134 coupled to the exterior surface 112 of the stent graft 100. In such an example, each of the plurality of retention flaps 134 has a fixed end 136 coupled to the exterior surface 112 of the stent graft 100 and a free end 138 directed toward the first end 104, such that each of the first plurality of barbs 122 are arranged between the fixed end 136 of the plurality of retention flaps 134 and the first end 104 of the stent structure 102. In one example, the free end 138 of each of the plurality of retention flaps 134 is biased toward the exterior surface 112 of the stent graft 100. In another example, the free end 138 of each of the plurality of retention flaps 134 covers the free end 126 of each of the first plurality of barbs 122 when the stent graft 100 is in the compressed condition, as shown in FIG. 5.

The plurality of retention flaps 134 may be made of a shape memory material, such as nitinol as an example. In one example, the plurality of retention flaps 134 are made from the same material as the plurality of barbs 122. In such an example, the plurality of retention flaps 134 may have a different diameter than the plurality of barbs 122 so that they have different resilient properties. For example, the diameter of each of the plurality of retention flaps may be less than the diameter of each of the plurality of barbs 122, such that the plurality of barbs 122 have a stronger flexing force than the plurality of retention flaps 134. In another example, the plurality of retention flaps 134 are made from different material than the plurality of barbs 122.

Further, as shown in FIG. 6, the free end 138 of each of the plurality of retention flaps 134 may be configured to flex away from the exterior surface 112 of the stent graft 100 to release the free end 126 of each of the first plurality of barbs 122 when the stent graft 100 transitions from the compressed condition to the expanded condition. In addition, as shown in FIG. 7, the free end 138 of each of the plurality of retention flaps 134 may rest adjacent to the exterior surface 112 of the stent graft 100 and the free end 126 of each of the first plurality of barbs 122 may extend away from the exterior surface 112 of the stent graft 100 when the stent graft 100 is in the expanded condition. In one example, the first plurality of barbs 122 may have a stronger flexing force than the plurality of retention flaps 134, such that when an outer sheath 142 of a delivery catheter is retracted, the plurality of retention flaps 134 automatically release the first plurality of barbs 122 to thereby engage the tissue of a target vessel or a previously-placed stent graft effectively establishing fixation.

Figure 8:
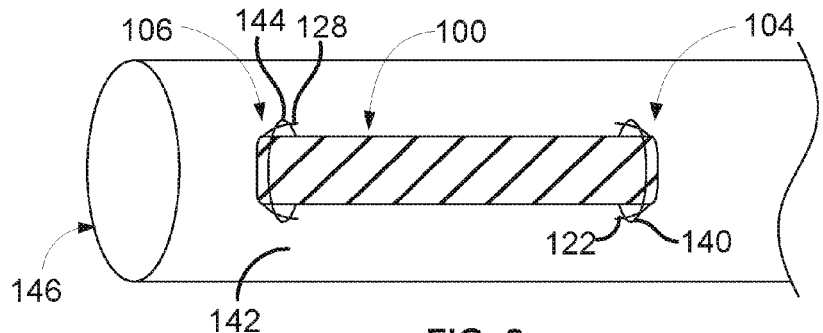
FIG. 8 is a side perspective view of a stent graft positioned within an outer sheath of a delivery catheter, according to an example embodiment.
Figure 9:
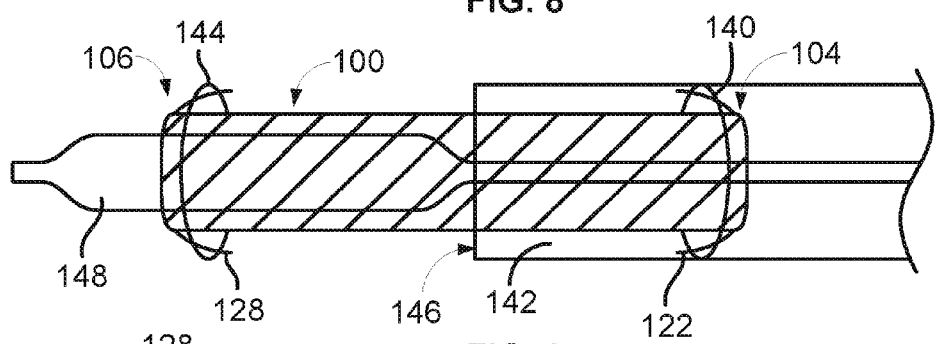
FIG. 9 is a side view of the stent graft with a balloon positioned in the second end of the stent graft, according to the example embodiment of FIG. 8.
Figure 10:
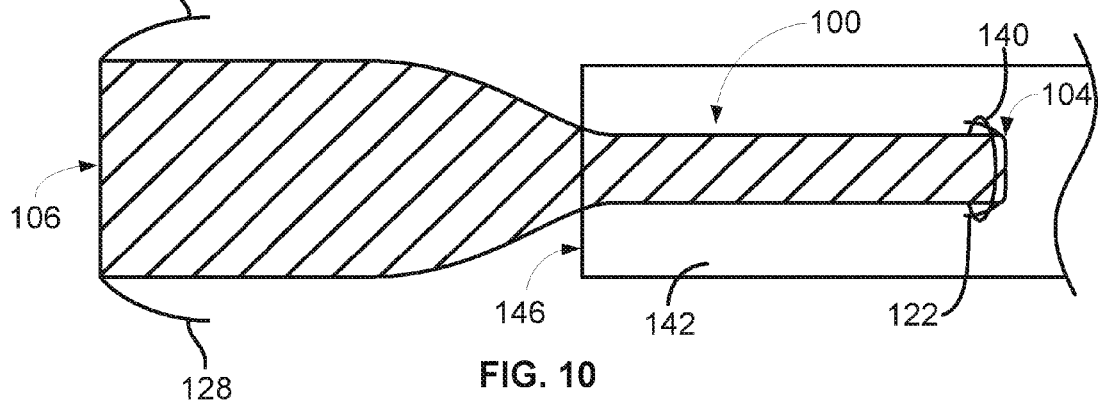
FIG. 10 is a side view of the stent graft with the balloon expanded in the second end of the stent graft, according to the example embodiment of FIG. 8.

In one example embodiment, as shown in FIGS. 8-10, the at least one restraint 110 comprises a first band 140 arranged to cover at least the free end 126 of each of the first plurality of barbs 122 when the stent graft 100 is in the compressed condition. The first band 140 may aid in retraction of a removable outer sheath 142 of a delivery catheter by preventing the first plurality of barbs 122 from catching on the outer sheath 142. Further, the at least one restraint 110 comprises a second band 144 arranged to cover at least the free end 132 of each of the second plurality of barbs 128 when the stent graft 100 is in the compressed condition. The second band 144 may aid in loading the stent graft 100 in the retractable outer sheath 142. However, if the stent graft 100 is loaded in the proximal end 146 of the outer sheath 142, then the second band 144 may not be needed to reduce friction with the outer sheath 142 due to the arrangement of the second plurality of barbs 128 towards the first end 104 of the stent structure 102 in the direction of sheath retraction. In these examples, the first band 140 and the second band 144 may each be at least 1 mm wide.

In operation, the stent graft 100 may be disposed within the outer sheath 142 of the delivery catheter with bands 140, 144 securing anchoring barbs 122, 128 on both the first and the second end 104, 106 of the self-expandable stent structure 102, as shown in FIG. 8. The outer sheath 142 is partially retracted and a balloon 148 is disposed within the second end 106 of the stent structure 102, as shown in FIG. 9. Next, the balloon 148 is expanded, causing the second band 144 to break, thereby causing the self-expandable stent structure 102 to expand to its expanded condition and the second plurality of barbs 128 to move radially outward. As shown in FIG. 10, the first end 104 of the stent structure 102 is still secured with the first band 140 and remains in the constrained condition. The balloon 148 may then be moved to the first end 104 of the stent structure 102 and expanded to fully transition the stent graft 100 to the expanded condition.

In another example, the first and second bands 140, 144 may be used to hold the barbs 122, 128 against the stent structure 102 allowing the stent graft 100 to be delivered without a delivery sheath or catheter. If a catheter or delivery sheath is not used, the first and second bands 140, 144 may permit a lower crossing profile than that offered by known stent graft delivery sheaths, which may be advantageous to enable the delivery of the stent graft 100 to smaller diameter vessels.

Figure 11:
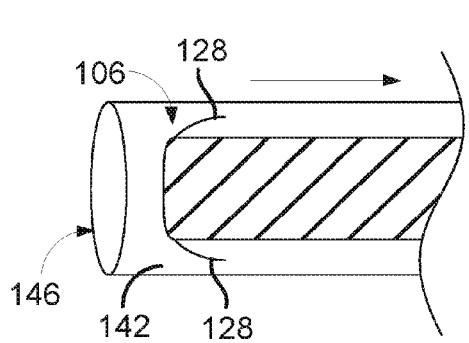
FIG. 11 is a side perspective view of a stent graft positioned within an outer sheath of a delivery catheter, according to an example embodiment.
Figure 12:
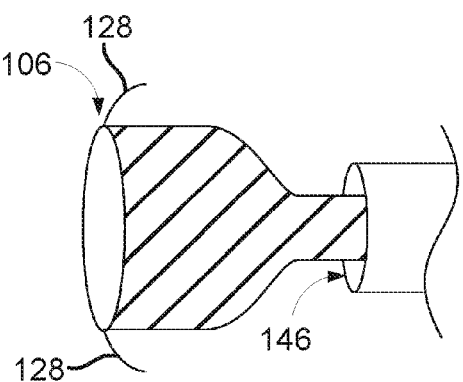
FIG. 12 is a side perspective view of the stent graft with the second end of the stent graft in an expanded condition, according to the example embodiment of FIG. 11.

In yet another example, as shown in FIGS. 11-12, the curved barbs 122, 128 can be held against the exterior surface 112 of the self-expandable stent structure 102 by an outer sheath 142 of a delivery catheter. As such, the outer sheath 142 of the delivery catheter acts as the restraint 110. Such a configuration is operational as a barb restraint if the barbs 122, 128 are located only on the second end 106 of the stent graft 100. This is because coupling barbs on the first end 104 of the stent graft 100 may result in puncture of the outer sheath 142 of the delivery catheter thereby interfering with effective deployment of stent graft 100. When the outer sheath 142 is pulled proximally to deploy the stent graft 100, the barbs 128 at the second end 106 of the stent structure 102 are configured to be released, as shown in FIG. 12.

In operation, an example method for placement of a stent graft 100 may include (a) introducing a guidewire into an arterial configuration via arterial access, (b) loading a delivery catheter containing the stent graft 100 according to the embodiments described above onto the guidewire, (c) moving the delivery catheter along the guidewire and introducing the delivery catheter into the arterial configuration via arterial access, and (d) deploying the stent graft 100 into at least one of the arterial configuration and a lumen of a previously-placed stent graft. In one example, deploying the stent graft 100 into at least one of the arterial configuration and a lumen of a previously-placed stent graft comprises retracting an outer sheath 142 of the delivery catheter from the stent graft 100. In one embodiment, the method may further include (e) expanding a balloon 148 in the lumen 108 of the self-expandable stent structure 102, and (f) decoupling the at least one restraint 110 from the stent graft 100, thereby permitting the self-expandable stent structure 102 to expand. In another example, the method may further include (g) in response to expanding the balloon 148 in the lumen 108 of the self-expandable stent structure 102, uncovering the free end 126 of each of the first plurality of barbs 122.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A stent graft, comprising:
a self-expandable stent structure having a first end and a second end, wherein the self-expandable stent structure defines a lumen;
a first plurality of anchoring projections coupled to an exterior surface of the stent graft adjacent to the first end of the self-expandable stent structure, wherein each anchoring projection of the first plurality of anchoring projections comprises a longitudinally arranged stent having a plurality of crimps, wherein each crimp of the plurality of crimps includes an acute peak extending radially away from the exterior surface of the stent graft in an expanded condition; and
at least one restraint coupled to the exterior surface of the stent graft in a compressed condition, wherein the at least one restraint covers at least a portion of the first plurality of anchoring projections in the compressed condition, and wherein the at least one restraint is configured to be broken to permit the stent graft to transition to the expanded condition.

2. The stent graft of claim 1, further comprising:
a second plurality of anchoring projections coupled to the exterior surface of the stent graft adjacent to the second end, wherein each anchoring projection of the second plurality of anchoring projections comprises a longitudinally arranged stent having a plurality of crimps.

3. The stent graft of claim 2, wherein the plurality of crimps of each of the longitudinally arranged stents extend radially outward when the stent graft is in the expanded condition.

4. The stent graft of claim 2, wherein the plurality of crimps of each of the longitudinally arranged stents extend radially outward a distance ranging from about 0.1 mm to about 3 mm from the exterior surface of the stent graft when the stent graft is in the expanded condition.

5. The stent graft of claim 2, wherein the plurality of crimps of each of the longitudinally arranged stents are flattened when the stent graft is in the compressed condition.

6. The stent graft of claim 2, wherein the first plurality of anchoring projections comprises at least three anchoring projections and wherein the second plurality of anchoring projections comprises at least three anchoring projections.

7. The stent graft of claim 2, wherein each of the first plurality of anchoring projections is structurally different than each of the second plurality of anchoring projections.

8. The stent graft of claim 1, wherein a diameter of the stent graft ranges from about 4 mm to about 30 mm.

9. The stent graft of claim 1, wherein the stent graft has a length ranging from about 20 mm to about 250 mm.

10. The stent graft of claim 1, wherein the at least one restraint is configured to remain coupled to the exterior surface of the stent graft after being broken.

11. The stent graft of claim 1, wherein the first plurality of anchoring projections are substantially flat with the exterior surface of the stent graft in the compressed condition, and wherein the first plurality of anchoring projections extend radially away from the exterior surface of the stent graft in the expanded condition.

* * * * *